(12) United States Patent
Wang et al.

(10) Patent No.: US 8,772,347 B2
(45) Date of Patent: Jul. 8, 2014

(54) USE OF A PHARMACEUTICAL COMPOSITION FOR PROMOTING PROLIFERATION AND/OR MIGRATION OF SKIN CELLS, AND FOR IMPROVING WOUND HEALING IN A SUBJECT

(75) Inventors: Hui-Min Wang, Taipei (TW); Chung-Yi Chen, Kaohsiung (TW); Chien-Chih Chiu, Kaohsiung (TW); Yi-Ting Chou, Taichung (TW)

(73) Assignee: Kaohsiung Medical University, Kaohsiung (TW)

( * ) Notice: Subject to any disclaimer, the term of this patent is extended or adjusted under 35 U.S.C. 154(b) by 118 days.

(21) Appl. No.: 13/445,451

(22) Filed: Apr. 12, 2012

(65) Prior Publication Data

US 2013/0123544 A1 May 16, 2013

(30) Foreign Application Priority Data

Nov. 16, 2011 (TW) .............................. 100141736 A

(51) Int. Cl.
*A61K 31/12* (2006.01)
*C07C 49/255* (2006.01)
*A61K 8/35* (2006.01)
*A61Q 19/08* (2006.01)
*A61K 8/97* (2006.01)

(52) U.S. Cl.
CPC . *A61K 8/35* (2013.01); *A61Q 19/08* (2013.01); *A61K 8/97* (2013.01)
USPC .......................................... 514/678; 568/308

(58) Field of Classification Search
USPC .......................................... 568/308; 514/678
See application file for complete search history.

(56) References Cited

PUBLICATIONS

Yamahara et al., "Vascular Dilatory Action of Artemisia Capiilaris Bud Extracts and Their Active Constituent", Journul of Ethnopharmacology, vol. 26, pp. 129-136, 1989.
Tjendraputra et al., "Effect of Ginger Constituents and Synthetic Analogues on yclooxygenase-2 Enzyme in Intact Cells", Bioorganic Chemistry, vol. 29, pp. 156-163, 2001.
Yoshimura et al., "Effects of all-trans retinoic acid on melanogenesis in pigmented skin equivalents and mnolayer culture of melanocytes", Journal of Dermatological Science, vol. 27, pp. S68-S75, Aug. 2001.
Afzal et al., "Ginger: An Ethnomedical, Chemical and Pharmacological Review", Freund Publishing House Ltd., vol. 18, pp. 159-190, 2001.
Koo et al., "Gingerols and Related Analogues Inhibit Arachidonic Acid-Induced Human Platelet Serotonin Release and Aggregation", Thrombosis Research, vol. 103, pp. 387-397, 2001.
Hinz et al., "Mechanical Tension Controls Granulation Tissue Contractile Activity and Myofibroblast Differentiation" ,American Journal of Pathology, vol. 159, No. 3, pp. 1009-1020, Sep. 2001.
Rolfe et al., "A Role for TGF-b1-Induced Cellular Responses during Wound Healing of the Non-Scarring Early Human Fetus?" Journal of Investigative Dermatology, vol. 127, pp. 2656-2667, 2007.
Shukla et al., "Cancer preventive properties of ginger: A brief review", Food and Chemical Toxicology, vol. 45, pp. 683-690, 2007.
Sumitra et al., "Emblica officinalis exerts wound healing action through up-regulation of collagen and extracellular signal-regulated kinases (ERK1/2)", Wound Rep Reg, vol. 17, pp. 99-107, 2009.
Cardinal et al., "Serial surgical debridement: A retrospective study on clinical outcomes in chronic lower extremity wounds", Wound Rep Reg, vol. 17, pp. 306-311, 2009.
Wang et al., "*Zingiber offi cinale* (Ginger) Compounds Have Tetracycline-resistance Modifying Effects Against Clinical Extensively Drug-Resistant *Acinetobacter baumannii*", Phytotherapy Research, vol. 24, pp. 1825-1830, Jun. 2010.
Chen et al., "Antiallergic Potential on RBL-2H3 Cells of Some Phenolic Constituents of *Zingiber officinale* (Ginger)", J. Nat. Prod., vol. 72, pp. 950-953, 2009.
Parekh et al., "Prostaglandin E2 differentially regulates contraction and structural reorganization of anchored collagen gels by human adult and fetal dermal fibroblasts", Wound Rep Reg, vol. 17, pp. 88-98 , 2009.
Taiwan Patent Office, Office Action, Patent Application Serial No. TW100141736, Oct. 1, 2013, Taiwan.
Warner et al., Curcumin and Ginger Extract Improves Abrasion Wound Healing in Damaged Skin, Faseb Journal, Apr. 2009, vol. 23, Meeting Abstract: 469.3.
Dasilva et al., MMP-1 Reduced in Organ Cultured Human Skin and Dermal Fibroblasts by Ginger and Curcumin, Faseb Journal, Apr. 2009, vol. 23, Meeting Abstract: 469.4.

*Primary Examiner* — Sikarl Witherspoon
(74) *Attorney, Agent, or Firm* — Rabin & Berdo, P.C.

(57) ABSTRACT

A method for promoting proliferation and/or migration of skin cells includes providing a composition containing a compound of formula (I) below; and administrating to the skin cells the composition. A method for improving wound healing in a subject includes providing a composition containing a compound of formula (I) below; and administrating to the subject the composition (I)

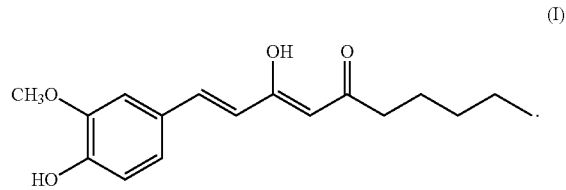

9 Claims, 14 Drawing Sheets

USE OF A PHARMACEUTICAL COMPOSITION FOR PROMOTING PROLIFERATION AND/OR MIGRATION OF SKIN CELLS, AND FOR IMPROVING WOUND HEALING IN A SUBJECT

CROSS REFERENCE

The application claims priority from Taiwan Patent Application No. 100141736 filed on Nov. 16, 2011, the contents of which are to be taken as incorporated herein by this reference.

FIELD OF THE INVENTION

The invention relates to a composition, a ginger extract, and a pharmaceutical composition using the same, and more particularly, to a composition and a ginger extract both for promoting proliferation and/or migration of skin cells, and a pharmaceutical composition using the same.

BACKGROUND OF THE INVENTION

Skin is the largest organ in the body of vertebrates, and composed of, from outside to inside, epidermis, dermis, and hypodermis. Keratinocytes in epidermis and fibroblasts in dermis are responsible for the body protection from mechanical or chemical damages and for wound healing. Wound healing, a complicated process, is a world-wide issue and costly for people of all ages. As proven by the Food and Drug Administration (FDA), there is merely one agent for would healing, all-trans retinoic acid. As described in literature, this agent is capable of promoting the expression of collagen and diminishing the amount of matrix metalloproteinase (MMP), and however, the side effects, such as skin stimulation or skin peeling, come along with the use of all-trans retinoic acid, which limits the applicability thereof. Steroid is another option for wound healing, but it makes collagen degraded and inhibits wound repair after being taken for a long period of time.

At the early stage of wound healing, fibroblasts around the wound migrate to start wound closure. With such a migration of the fibroblasts, the wound closure is initiated and newborn tissues resist the differentiation of the fibroblasts. See Wound Repair Regen 2009; 17: 88-98 and Am J Pathol 2001; 159: 1009-20. Such a phenomenon is characterized by the expression profiles of skin cells and growth factors, and the change of extracellular matrix (ECM). The proliferation and migration of the keratinocytes and fibroblasts benefit the progress of wound healing. Transforming growth factor-β (TGF-β), vascular endothelial growth factor (VEGF), and platelet-derived growth factor-αβ (PDGF-αβ) have been proven as the main growth factors involved in the proliferation of skin cells. ECM is sited around the skin cells and within connective tissues for strengthening the cellular structure and mediating the cellular behavior. Collagen is abundant in ECM and the richest protein in connective tissues.

TGF-β is involved in cell differentiation, adhesion, proliferation, and migration, and ECM precipitation. During wound healing, TGF-β produced by keratinocytes, fibroblasts, macrophages, and platelets is significant for connective tissue regeneration, inflammation, and epidermis reformation. See J Invest Dermatol 2007; 127: 2656-67. Generally, it is recognized that TGF-α is able to mediate wound contract, cell migration, and scar formation. VEGF, also called vascular permeability factor, is secreted by keratinocytes, fibroblasts, macrophages, neutrophils, platelets, endothelial cells, and smooth muscle cells and is a mediating factor for endothelial cell migration, proliferation, and penetration during angiogenesis. PDGF-αβ plays a key role in the process of skin cell proliferation. As such, it is thought that these growth factors have effects on skin cell proliferation or wound healing.

MMP, comprising over 20 different zinc peptidases of the metzincin superfamily, is for the maintenance and turnover of macromolecules of ECM, such as collagen. MMP-1, also called interstitial collagenase, initiates the degradation of ECM and cooperates with other MMP to promote the degradation of collagen. Phorbol 12-myristate 13-acetate (PMA), known as an activator for protein kinase C, phosphorylates c-Jun N-terminal kinase (JNK), and extracellular signal-regulated kinase (ERK) to produce MMP-1, and inhibits tissue inhibitor of metalloproteinase-1 (TIMP-1). The reconstruction and synthesis of collagen in ECM are of importance for cell proliferation and wound healing.

Ginger is the rhizome of the plant *Zingiber officinale*, and has been widely used for food flavoring. As documented in Chinese medicine, ginger has been used as a treatment for allergy, asthma, constipation, diabetes, gingivitis, nervous diseases, rheumatism, stroke, toothache, and anti-microorganism infection. See Drug Metabol Drug Interact 2001; 18: 159-90, J Nat Prod 2009; 72: 950-3, Food Chem Toxicol 2007; 45: 683-90, and Phytother Res 2010a; 24: 1825-30. Moreover, literature has said that ginger has been used for treatment of chemotherapy-associated nausea, suppression of platelet aggregation, and inhibition of cyclooxygenase and nitric oxide synthase. See Thromb Res 2001; 103: 387-97, Wound Repair Regen 2009; 17: 99-107, Bioorg Chem 2001; 29: 156-63, and J Ethnopharmacol 1989; 26: 129-36. Other literature has repeatedly reported that ginger extract has positive biological functions on wound healing either in vivo or in vitro. See Wound Repair Regen 2009; 17: 306-6 and J Dermatol Sci 2001; Suppl 1: S68-S75.

As described above, research up to now shows that ginger has effects on the promotion of skin cell proliferation and migration. Therefore, an agent for wound healing is desirable and is needed to be provided and produced synthetically in the near future, if the active component for the promotion of skin cell proliferation and migration in ginger is discovered.

SUMMARY OF THE INVENTION

In one aspect, the invention provides a composition for promoting proliferation and/or migration of skin cells, which comprises a compound of formula (I):

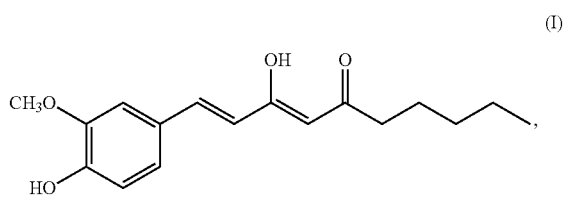

or a pharmaceutically acceptable salt or ester thereof as an active component.

In another aspect, the invention provides a ginger extract for promoting proliferation and/or migration of skin cells, which comprises a compound of formula (I):

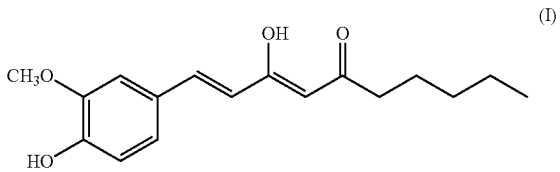

as an active component.

In a further aspect, the invention provides a pharmaceutical composition for wound healing, which comprises a compound of formula (I):

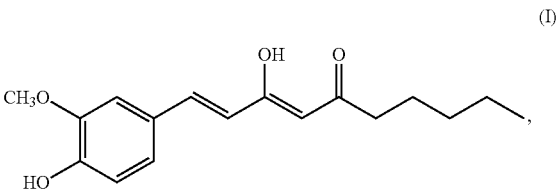

or a pharmaceutically acceptable salt or ester thereof as an active component.

In yet another aspect, the invention provides a ginger extract for wound healing, which comprises a compound of formula (I):

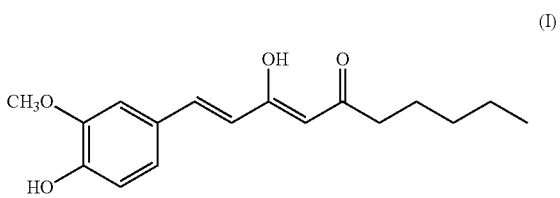

as an active component.

The detailed description and preferred embodiment of the invention will be set forth in the following content, and provided for people skilled in the art so as to understand the characteristic of the invention.

DETAILED DESCRIPTION OF THE INVENTION

The invention is related to a composition for promoting the proliferation and/or migration of skin cells. This composition includes a compound of formula (I):

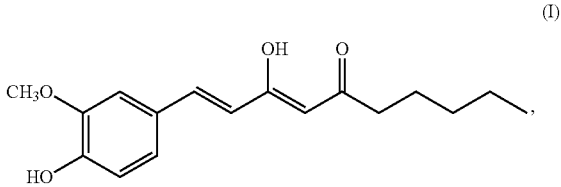

or a pharmaceutically acceptable salt or ester thereof as an active component. The compound of formula (I) is scientifically named 6-dehydrogingerdione (6-DG), and thus it is entitled such a name thereinafter.

After experiment, it is found that the composition of the invention is able to inhibit the activity and/or synthesis of MMP. Specifically, the composition of the invention is able to inhibit the activity and/or synthesis of MMP-1, MMP-3, MMP-9, and/or MMP-10 so as to prevent and reduce the degradation of collagen. In such a way, skin cells are proliferated and migrated.

It is further found that the composition of the invention is able to repress the phosphorylation of mitogen-activated protein kinase (MAPK). Specifically, the composition of the invention is able to repress the phosphorylation of JNK, ERK, and/or p38. As described in Biofactor 2008; 33: 121-8, phosphorylated MAPK can induce the amount of MMP. Therefore, the composition of the invention is able to inhibit the phosphorylation of MAPK and reduce the amount of MMP so as to prevent and reduce the degradation of collagen and make the proliferation and migration of skin cells.

It is still further found that the composition of the invention is able to induce the expression of growth factors related to skin cell proliferation so as to make the skin cells proliferated and/or migrating. Specifically, the composition of the invention is able to induce the expression of TGF-β, VEGF, and PDGF-αβ, and makes the skin cells proliferated and/or migrating.

Figure 1:
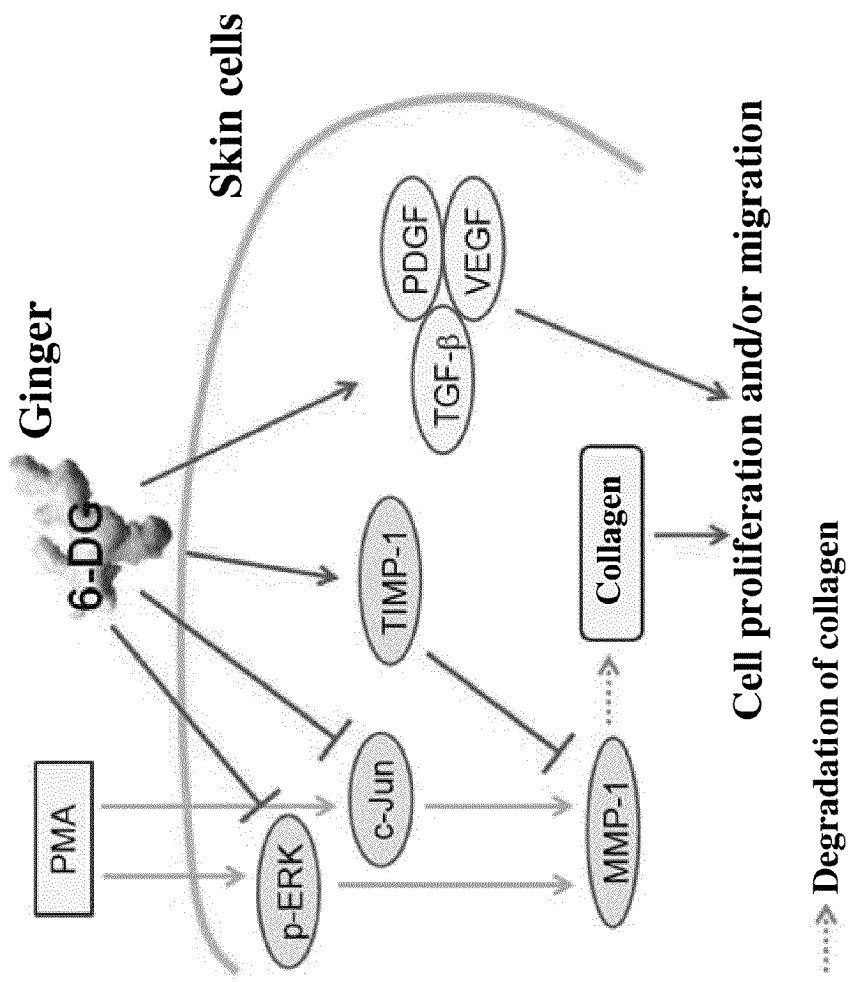
FIG. 1 is a schematic view showing the mechanism of 6-DG for skin cells.

As shown in FIG. 1, the composition of the invention has the following characteristics including: (1) directly inhibiting the activity and/or synthesis of MMP to reduce the collagen degradation; (2) indirectly inhibiting the MMP activity and/or synthesis by repressing the phosphorylation of MAPK to reduce the collagen degradation; and (3) promoting the expression of growth factors related to skin cell proliferation. According to these characteristics, the composition of the invention satisfies the purpose of skin cell proliferation and migration, and may be used for restoring, improving, and/or repairing skin, such as anti-aging, prevention of wrinkles, prevention of skin relaxation, improvement of the texture of skin, and wound healing. In one embodiment, the composition of the invention may be used for wound healing.

The term "a pharmaceutically acceptable salt or ester," described in this content, academically refers to a pharmaceutically acceptable salt or ester which can promote the proliferation and/or migration of skin cells. For example, the salt may be a sodium salt, a potassium salt, a magnesium salt, an aluminum salt, a lithium salt, a calcium salt, an ammonium salt, an acetic salt, a carbonate salt, or a phosphoric salt. For example, the ester may be methyl ester, ethyl ester, propyl ester, butyl ester, pentyl ester, acetic acid methyl ester, or acetic acid ethyl ester.

The composition of the invention may be extracted from, but not limited to, ginger. The composition of the invention may be obtained by extraction disclosed in J Nat Prod 2009; 72: 950-3. Briefly, the composition of the invention may be a crude extract which is extracted from ginger by a polar solvent. Preferably, the polar solvent may be methanol, ethanol, propanol, glycol, butanol, butanediol, or chloroform-methanol. The weight ratio of the polar solvent to the ginger may range from 1.0:1.0 to 10.0:1.0, and preferably is of 2.0:1.0.

As the application of the composition of the invention, the crude extract may be further purified. For example, the crude extract may be separated into fractions by being eluted in chromatography with a solvent, and thereafter, an optimal fraction containing 6-DG is selected through analysis. In addition, the optimal fraction may be purified again by being eluted in chromatography with another solvent.

As the application of the composition of the invention, the crude extract or the fractions may be dried through, such as freeze drying or reduced pressure drying, to remove the solvent therein for reducing biological toxicity of the composition.

It is noticeable that the composition of the invention may be of any suitable forms without any limitations. For example, the composition may be in a form of emulsion, cream, or gel for external use, such as cosmetics, skin care products, or ointments. Also, the composition may be in the form of food for swallowing or drinking, such as health foods or beauty drinks. Moreover, the composition may be in the form of a common pharmaceutical form, such as a tablet, a capsule, a granule, a powder, a fluid extract, a solution, a syrup, a suspension, an emulsion, a tincture, an intravenous injection, a powder injection, a suspension injection, or a powder-suspension injection.

It is further noticeable that the 6-DG amount of the composition of the invention may be adjusted based on treated subjects and purposes. The 6-DG amount also may be adjusted according to frequency of use. For example, when the composition is used for wound healing, the 6-DG amount may range from 2 to 50 µM, preferably from 2 to 25 µM, and more preferably, is of 2 µM, based on the total volume of the composition. Actually, the 6-DG amount of the composition of the invention may be of any concentration as long as it has no adverse influence on skin cells.

The invention is further related to a ginger extract for promoting the proliferation and/or migration of skin cells. This extract includes 6-DG as an active component. As described above, the extract is able to reduce the degradation of collagen, reaches the purpose of the skin cell proliferation and migration, and so may be used for restoring, improving, and/or repairing skin, such as anti-aging, prevention of wrinkles, prevention of skin relaxation, improvement on skin texture, and wound healing. In one embodiment, the extract of the invention may be used for wound healing.

The extract of the invention may be yielded by extraction disclosed in J Nat Prod 2009; 72: 950-3. Briefly, the extract of the invention may be a crude extract which is extracted from ginger by a polar solvent. Preferably, the polar solvent may be methanol, ethanol, propanol, glycol, butanol, butanediol, or chloroform-methanol. The polar solvent and ginger have a weight ratio ranging from 1.0:1.0 to 10.0:1.0, and preferably being of 2.0:1.0.

As the application of the extract of the invention, the crude extract may be further purified. For example, the crude extract may be separated into fractions by being eluted in chromatography with a solvent, and then, an optimal fraction containing 6-DG is chosen through analysis. In addition, the optimal fraction may be purified again in chromatography with another solvent.

As the application of the extract of the invention, the crude extract or the fractions may be dried through, such as freeze drying or reduced pressure drying, to remove the solvent therein for reducing the biological toxicity of the extract.

It is noticeable that the 6-DG amount of the extract of the invention may be adjusted according to treated subjects and purposes. The 6-DG amount also may be adjusted based on usage frequencies. For example, when the extract is used for wound healing, the 6-DG amount may range from 2 to 50 µM, and preferably from 2 to 25 µM, and more preferably, is of 2 µM, based on the total volume of the extract. Actually, the 6-DG amount of the extract of the invention may be of any concentration as long as it has no adverse influence on skin cells.

The invention is further related to a composition for wound healing. This composition includes 6-DG, or a pharmaceutically acceptable salt or ester thereof as an active component. As described above, the composition is able to reduce the degradation of collagen and reaches the purpose of the proliferation and migration of skin cells, so that it may be used for wound healing.

The invention is further related to a ginger extract for wound healing. This extract includes 6-DG as an active component. As described above, the extract is able to reduce the degradation of collagen and reaches the purpose of skin cell proliferation and migration, so that it may be used for wound healing.

The following examples are offered to further illustrate the invention.

EXAMPLE 1

Preparation of 6-DG

Ginger, purchased from a supermarket, is air-dried and chipped. Following the extraction provided in J Nat Prod 2009; 72: 950-3, the air-dried and chipped ginger (25.6 kg) is extracted repeatedly with chloroform-methanol (50 L) at room temperature and a crude extract is yielded. The crude extract is evaporated, added into silica gel (3.8 kg, 70-230 mesh) with gradients of n-hexane-chloroform, and eluted with different concentration of chloroform-methanol to yield 20 fractions. The 8th fraction, eluted with chloroform-methanol (60:1), is purified again in silica gel with chloroform-methanol and a composition is acquired. Finally, the composition is identified to have 6-DG by spectroscopic analysis.

EXAMPLE 2

Culture of Skin Cells

Skin cells are cultured following the method provided in Exp Dermatol 2011; 20: 242-8. Human skin fibroblasts are derived from Chung-Ho Memorial Hospital, Kaohsiung Medical University, Taiwan, ROC, and incubated in Dulbecco's Modified Eagle Medium including 10% fetal calf serum, 100 μg/ml streptomycin, and 250 ng/ml amphotericin B. Human keratinocytes are isolated from foreskin primary culture and cultured in Keratinocyte-SFM Medium supplemented with Bovine Pituitary Extract and EGF. All of these cells are incubated at 37° C. in a humidified incubator with 5% $CO_2$ atmosphere.

EXAMPLE 3

Proliferation of Skin Cells 3-(4,5-cimethylthiazol-2-yl)-2,5-diphenyl tetrazolium bromide assay (MTT assay) is performed to analyze the effect on the proliferation of skin cells treated with different 6-DG concentration (dissolved in DMSO). Firstly, 6-DG of different concentration is seeded in a 96-well culture dish cultured with skin cells and incubated for 24 hr. MIT solution (5 mg/ml, dissolved in PBS) is added into the dish and incubated again at 37° C. for 2 hr. Medium in the dish is removed, 0.05 ml DMSO is added to the dish, and then the dish is shaken in a dark position for 20 min. Finally, the OD value of each well of the dish is calculated by 595 nm-wavelength light (UV-vis, BioTek, USA). Considering whether DMSO has effect on the skin cell proliferation or not, skin cells treated with DMSO are used as a control. In this example, it is found that DMSO has no effect on the skin cell proliferation.

Figure 2A:
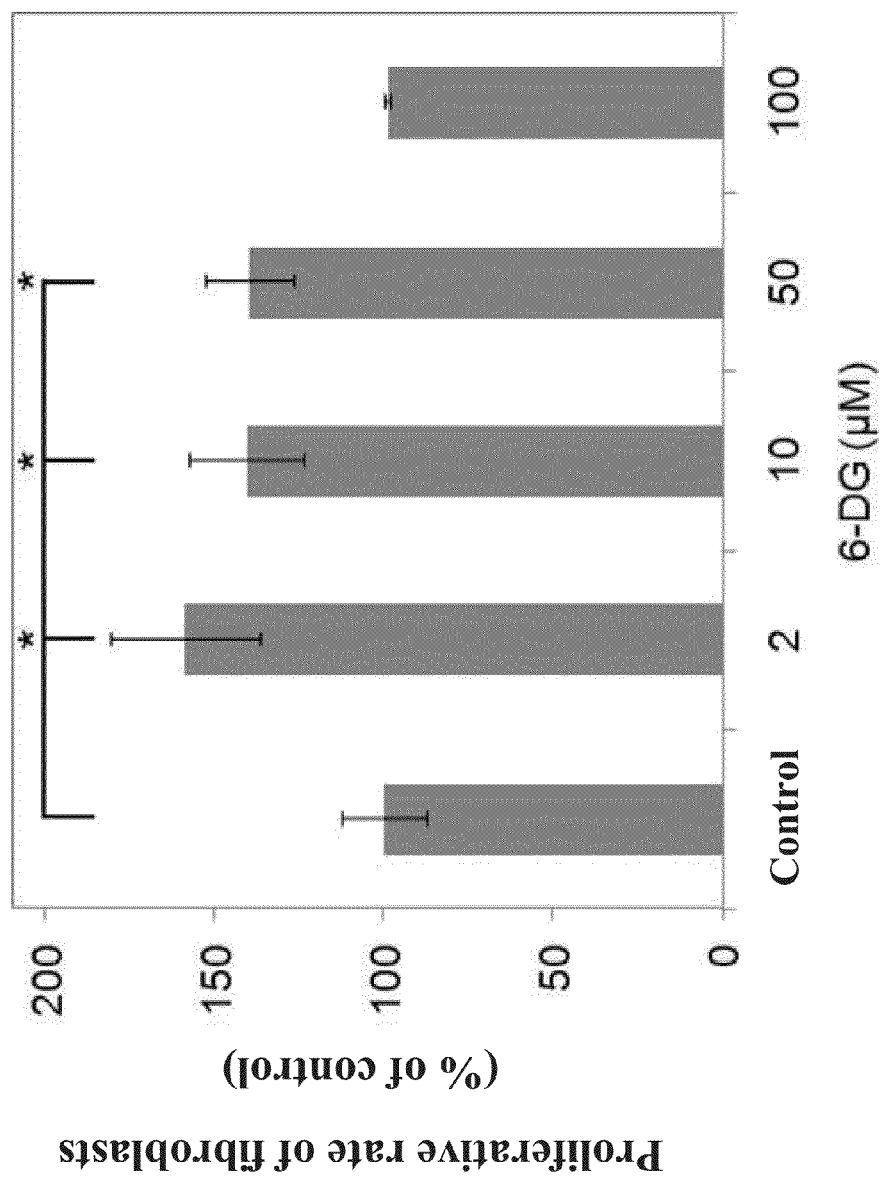
FIG. 2(A) is a bar chart illustrating the proliferative rate of human fibroblasts treated with different concentration of 6-DG.
Figure 2B:
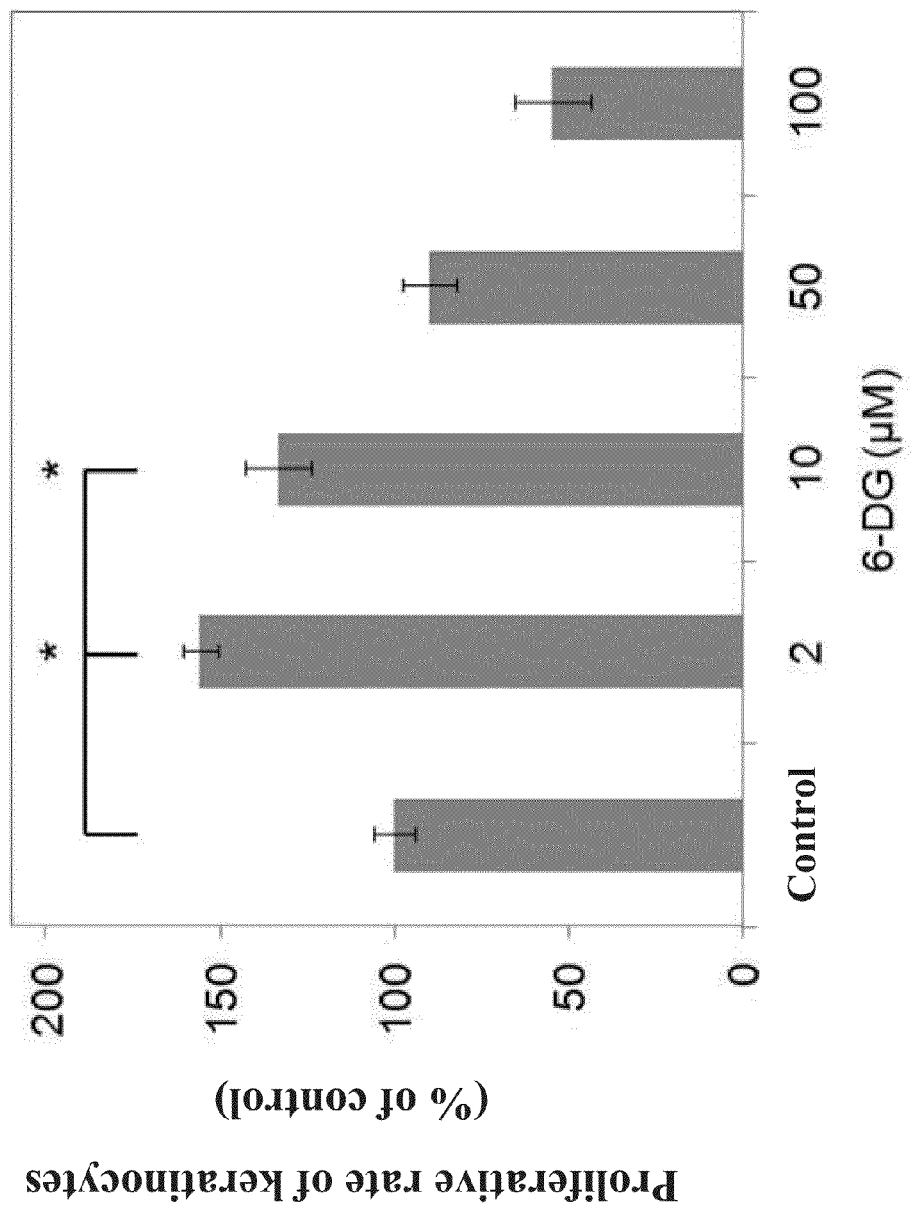
FIG. 2(B) is a bar chart illustrating the proliferative rate of human keratinocytes treated with different concentration of 6-DG.

As shown in FIG. 2(A), compared with control, the human fibroblasts treated with 2 μM 6-DG or 50 μM 6-DG are obviously proliferated, but the human fibroblasts treated with 100 μM 6-DG are not obviously proliferated. As shown in FIG. 2(B), compared with control, the human keratinocytes treated with 2 μM 6-DG or 50 μM 6-DG are also obviously proliferated, but the human keratinocytes treated with 100 μM 6-DG are not obviously proliferated.

As the foregoing results, 6-DG is proven to able to promote the skin cell proliferation, and has an effective concentration of 2-50 μM, based on the volume of the composition.

EXAMPLE 4

Expression of Growth Factors

Enzyme-linked immunoassay (ELISA) is performed to analyze the effect on the growth factor expression of skin cells treated with different 6-DG concentration (dissolved in DMSO). Firstly, 6-DG of different concentration is incubated in a 6-well culture dish with skin cells cultured in a conditioned medium for 24 hr. Supernant of the conditioned medium is collected for analyzing the concentration of TGF-β, VEGF, and PDGF-αβ following the directions provided by DuoSet ELISA development kits (R&D Systems, USA). With regard to whether DMSO has effect on the growth factor expression or not, skin cells treated with DMSO are used as a control. In this example, it is found that DMSO has no effect on the growth factor expression.

As shown in Tables 1 to 2, compared with untreated control (skin cells untreated) and control, the medium for human fibroblasts and human keratinocytes contains larger amount of TGF-β, VEGF, and PDGF-αβ after being treated with 6-DG.

TABLE 1

| | Fibroblasts | | | |
|---|---|---|---|---|
| | Untreated | | 6-DG (μM) | |
| | control | Control | 2 | 10 |
| TGF-β (pg/ml) | 778.3 ± 15.6 | 778.3 ± 3.3 | 984.5 ± 21.6 | 1003.3 ± 24.0 |
| PDGF-αβ (pg/ml) | 2.5 ± 0.1 | 1.7 ± 0.2 | 7.1 ± 0.1 | 5.3 ± 0.1 |
| VEGF (pg/ml) | 287.0 ± 1.1 | 279.5 ± 12.9 | 432.0 ± 14.6 | 294.5 ± 14.6 |

TABLE 2

| | Keratinocytes | | | |
|---|---|---|---|---|
| | Untreated | | 6-DG (μM) | |
| | control | Control | 2 | 10 |
| TGF-β (pg/ml) | 665.4 ± 8.2 | 642.3 ± 20.1 | 822.8 ± 15.3 | 768.0 ± 9.6 |
| PDGF-αβ (pg/ml) | 2.20 ± 0.1 | 1.46 ± 0.2 | 5.84 ± 0.2 | 4.55 ± 0.1 |
| VEGF (pg/ml) | 250.7 ± 6.3 | 234.5 ± 11.7 | 344.3 ± 9.5 | 292.8 ± 7.3 |

As the foregoing results, 6-DG is proven to able to promote the growth factor expression of skin cells, such as TGF-β, VEGF, and PDGF-αβ.

EXAMPLE 5

Migration of Skin Cells

An assay disclosed in Process Biochemistry 2010; 45:1865-72 is performed to analyze the effect on migration of skin cells treated with different 6-DG concentration (dissolved in DMSO). $5 \times 10^5$ skin cells are seeded in a 12-well culture dish and grown to complete confluence. Prior to adding 6-DG of different concentration to the dish, a clean 1-nm-wide would area is created on the skin cells. The wound area is photographed using an inverted phase-contrast microscopy (TE2000-U; Nikon, Tokyo, Japan) equipped with NIS-Elements software (Nikon), and the skin cell migration in the wound area is calculated by the free software "TScratch" (www.cse-lab.ethz.ch/software.html). Considering whether DMSO has effect on the skin cell migration or not, skin cells treated with 0.5% DMSO are used as a control. In this example, it is found that DMSO has no effect on the skin cell migration.

Figure 3A:
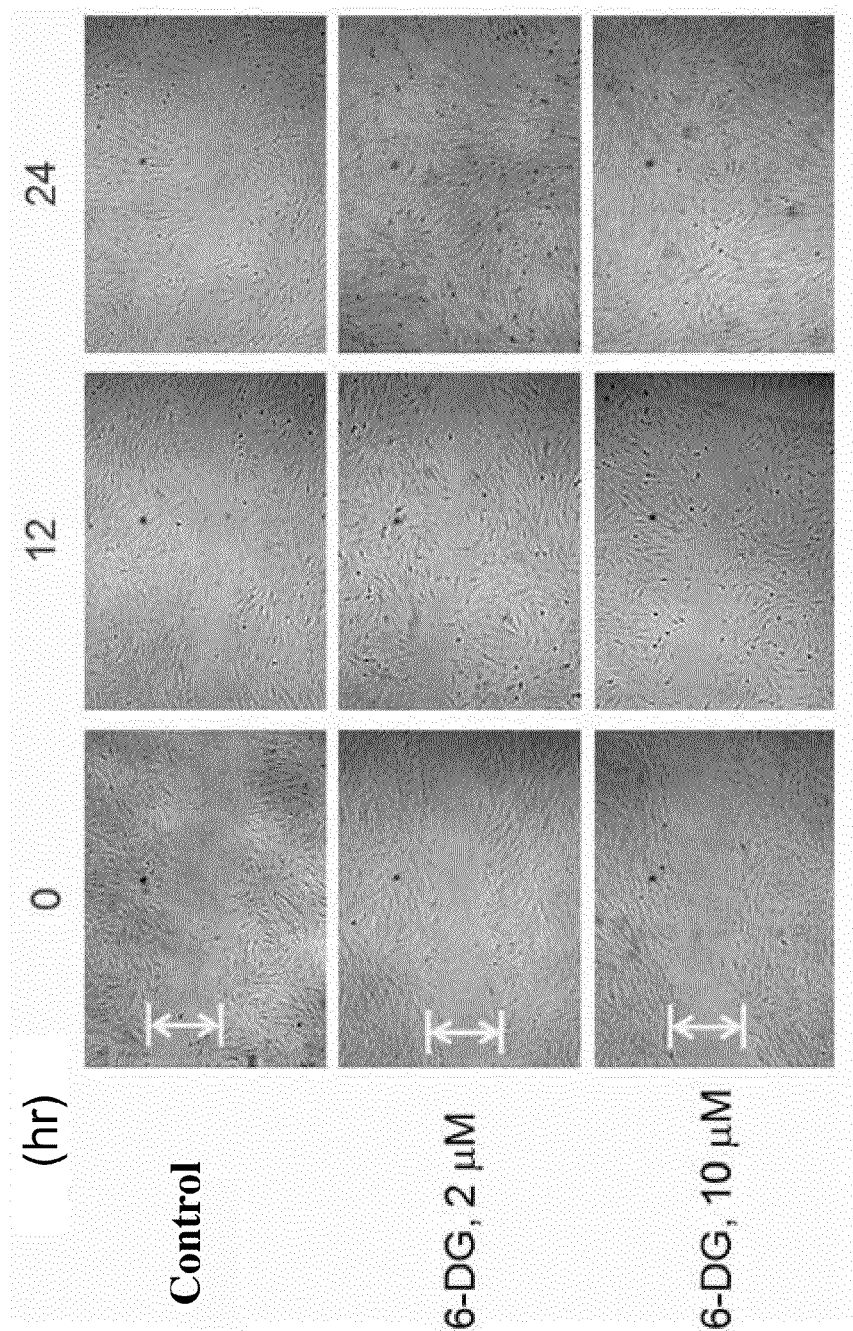
FIG. 3(A) is a picture showing the migration of human fibroblasts treated with different concentration of 6-DG.
Figure 3B:
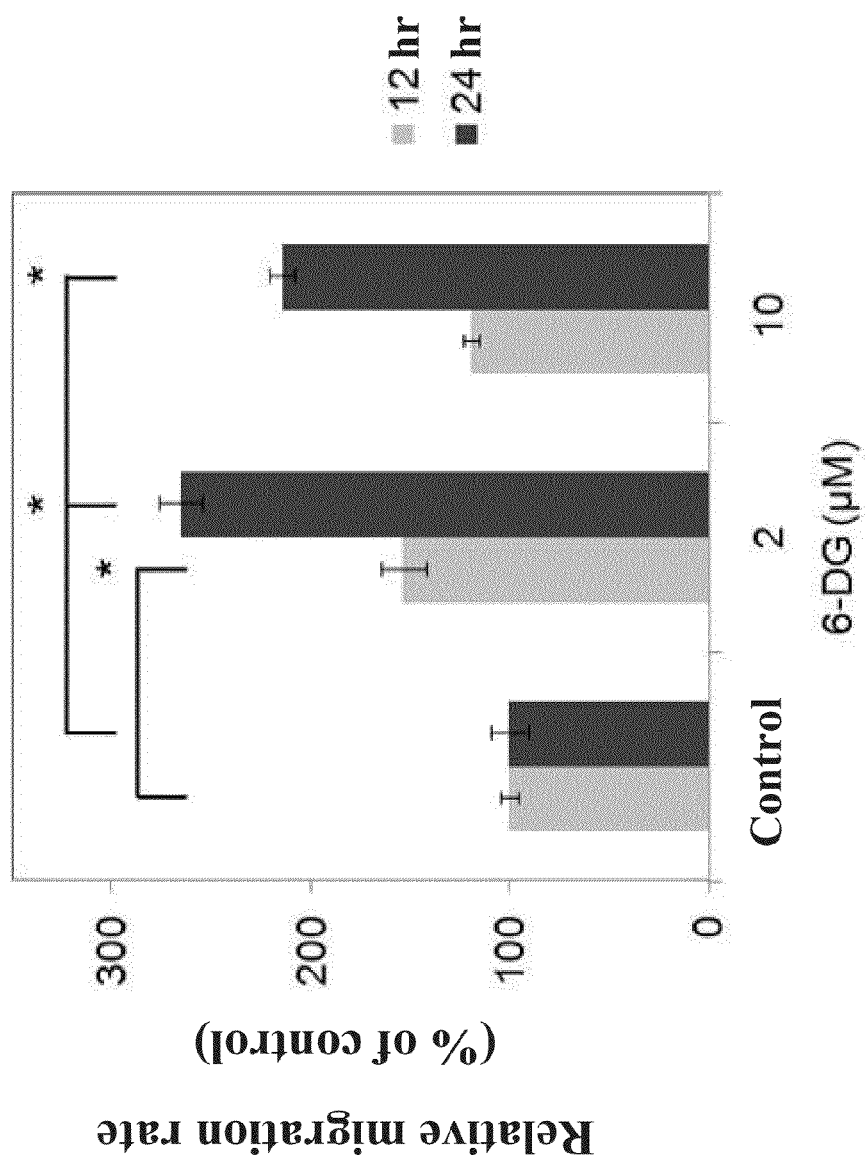
FIG. 3(B) is a bar chart illustrating the migration rate of human fibroblasts treated with different concentration of 6-DG.

As shown in FIGS. 3(A) to 3(B), compared with control, the human fibroblasts treated with 6-DG obviously migrate to the wound area, and the phenomenon that the human fibroblasts migrate to the wound area after being treated with 2 μM for 24 hr is more obvious. However, the phenomenon the human fibroblasts migrate to the wound area after being treated with 10 μM is less obvious than that after being treated with 2 μM.

Figure 3C:
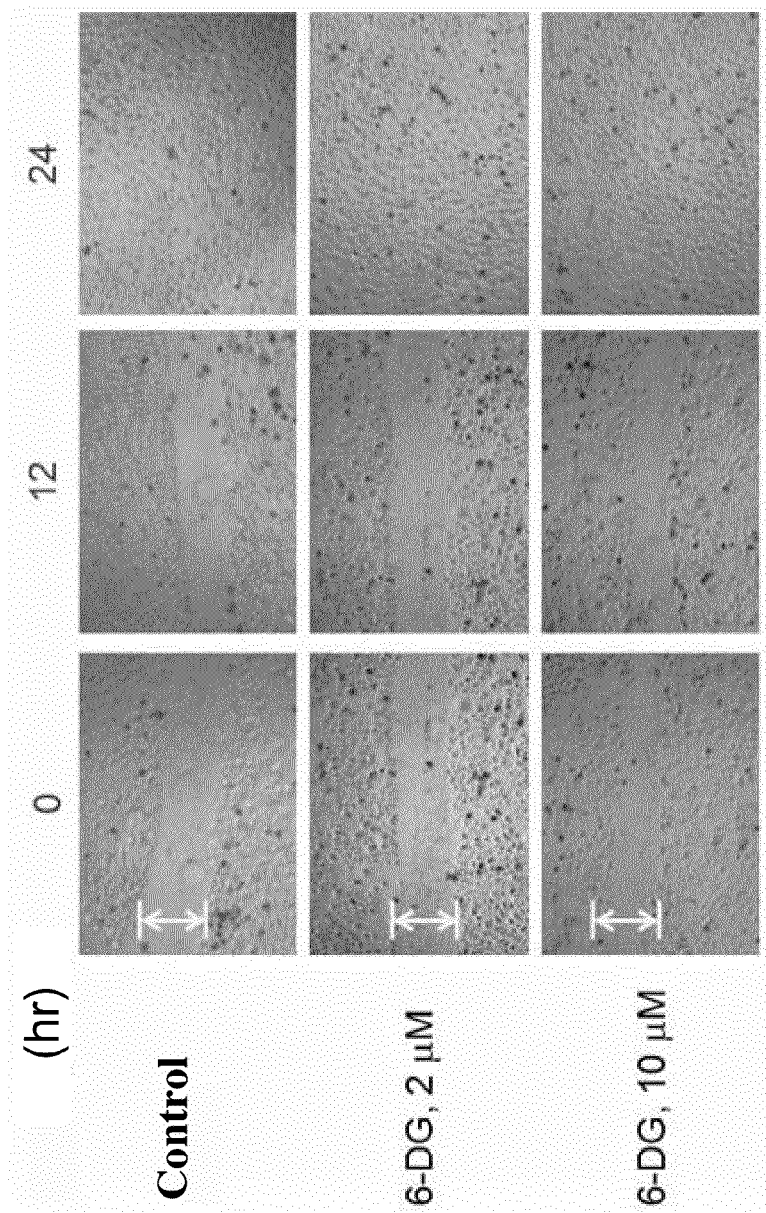
FIG. 3(C) is a picture showing the migration of human keratinocytes treated with different concentration of 6-DG.
Figure 3D:
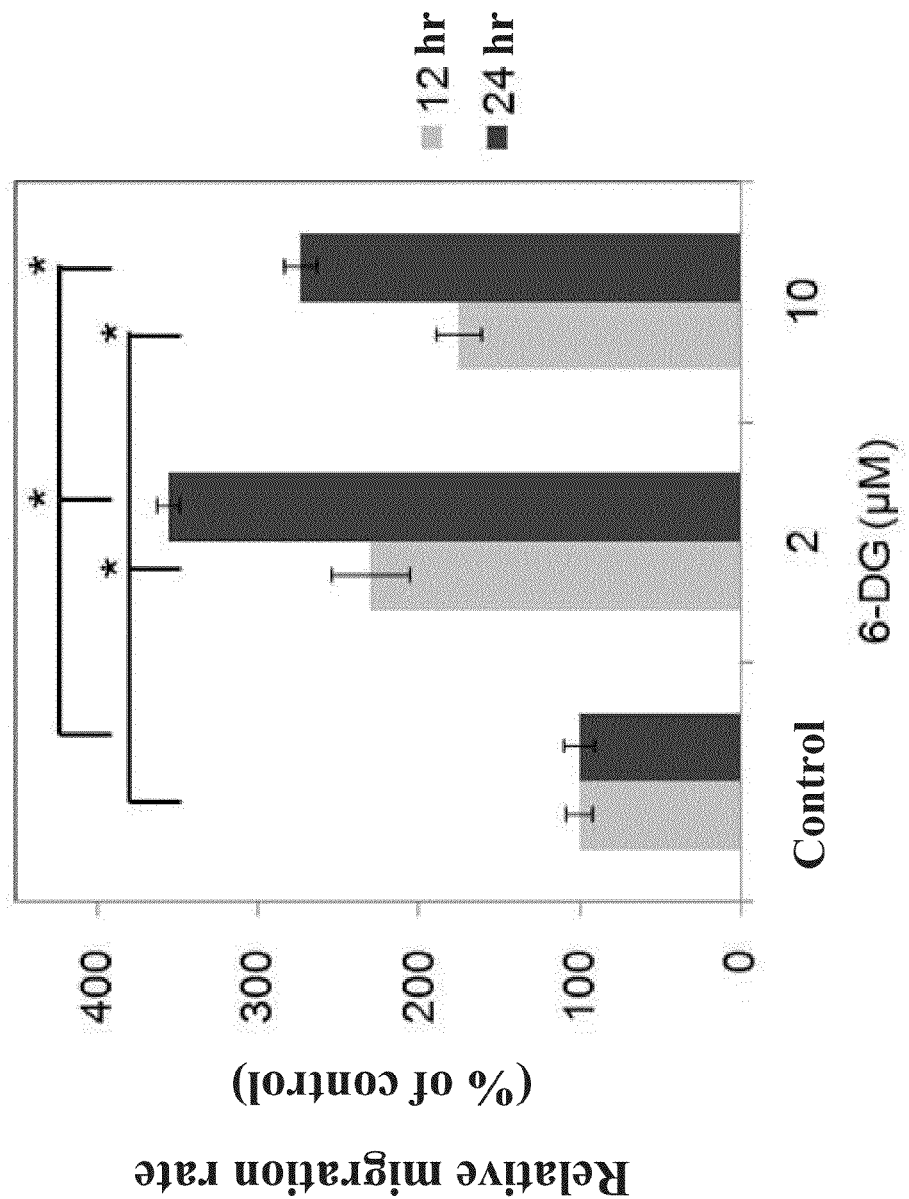
FIG. 3(D) is a bar chart illustrating the migration rate of human keratinocytes treated with different concentration of 6-DG.

As shown in FIGS. 3(C) to 3(D), compared with control, the human keratinocytes treated with 6-DG obviously migrate to the wound area, and the phenomenon that the human keratinocytes migrate to the wound area after being treated with 2 μM for 24 hr is more obvious. However, the phenomenon the human keratinocytes migrate to the wound area after being treated with 10 μM is less obvious than that after being treated with 2 μM.

As the foregoing results, 6-DG is proven to able to promote the migration of skin cells, and has an effective concentration of 2-50 µM, based on the volume of the composition.

EXAMPLE 6

Western Blotting

Signal transduction of skin cells treated with 6-DG is studied. Firstly, 6-DG of different concentration is incubated with $1\times10^6$ human fibroblasts. After being incubated for 24 hr, the human fibroblasts are washed twice with phosphate-buffered saline (PBS), and then lysed by a lysis buffer containing 50 mM Tris-HCl, pH7.5, 137 mM sodium chloride, 1 mM EDTA, 1% Nonidet P-40, 10% glycerol, 0.1 mM sodium orthovanadate, 10 mM sodium pyrophosphate, 20 mM β-glycerophosphate, 50 mM sodium fluoride, 1 mM phenylmethysulfonyl fluoride, 2 mM leupeptin, and 2 µg/ml aprotinin. A cell extract having the lysed human fibroblasts is separated by a centrifugal force of 10,000 g at 4° C., and supernant of the cell extract is collected for determining protein concentration using Bicinchoninic acid protein assay kit (Pierce, Rockford, Ill., USA). Equal concentration of protein in the supernant is separated by SDS-PAGE, and then blotted to a PVDF membrane (PALL Life Science, Ann Arbor, Mich., USA). After being blocked for 1 hr in phosphate-buffered saline & tween (PBST) containing 5% non-fat milk, primary antibodies are added to the membrane. The membrane is washed with PBST twice, and next secondary antibodies against the primary antibodies are added to the membrane. Finally, signals on the membrane are visualized by enhanced chemiluminescence substrate (PerkinElmer, USA). As the description of "BACKGROUND OF THE INVENTION," it is said that PMA, an activator for protein kinase C, phosphorylates JNK and ERK to produce MMP-1 and inhibits TIMP-1. For further confirming the effect on signal transduction of skin cells treated with 6-DG, the human fibroblasts are incubated with 20 ng/ml PMA prior to being treated with 6-DG.

Figure 4A:
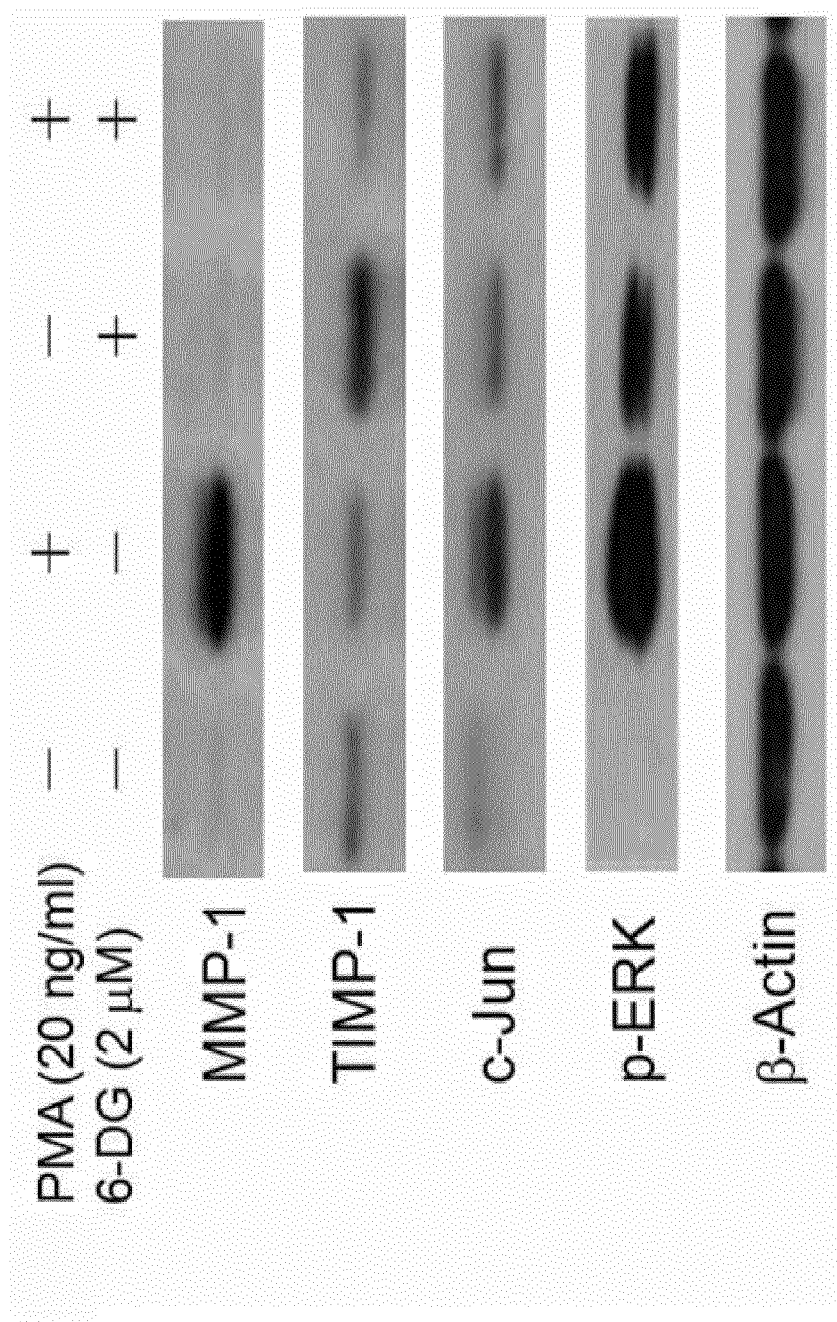
FIGS. 4(A) to 4(B) are pictures showing the signal transduction-related protein amount of skin cells treated with different concentration of 6-DG.
Figure 4B:
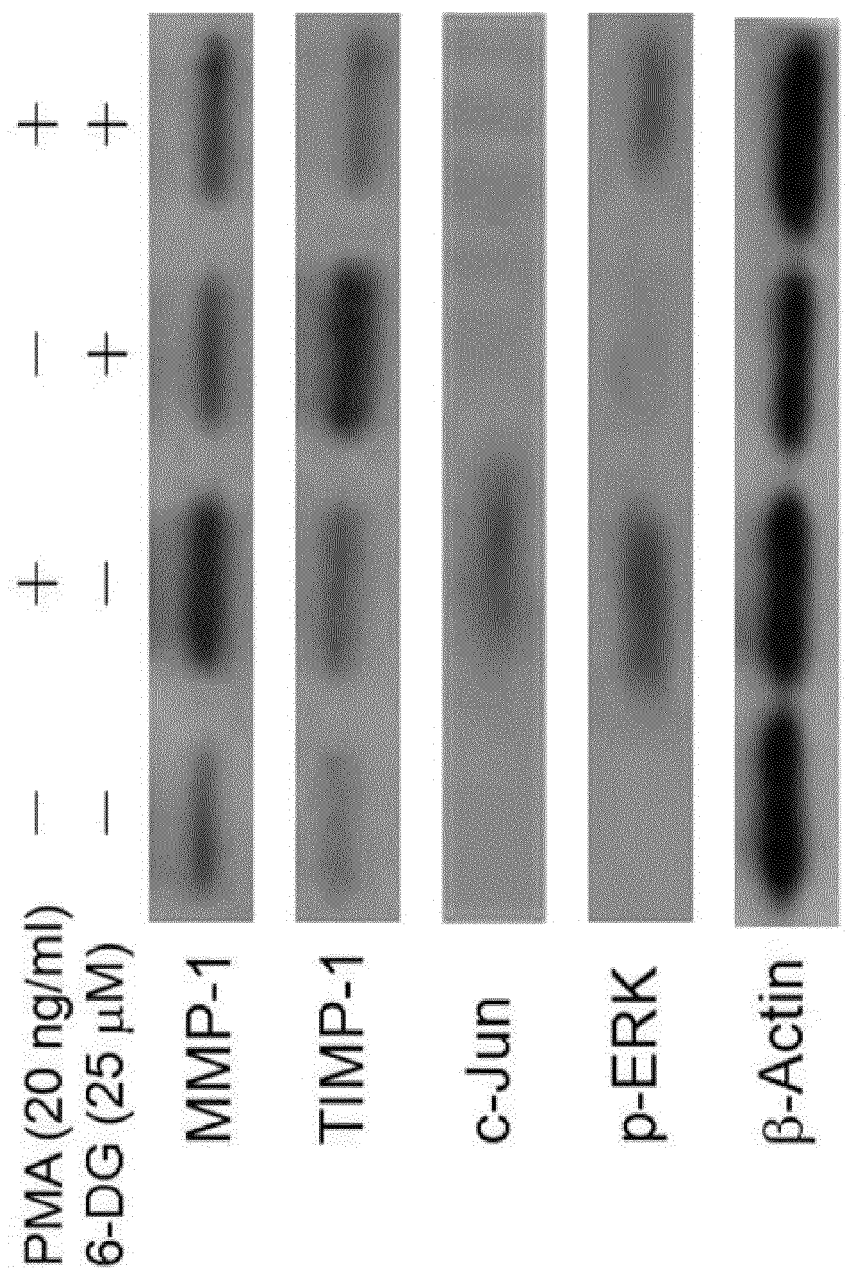

As shown in FIGS. 4(A) to 4(B), compared with the fibroblasts untreated (line 1), the fibroblasts treated with 6-DG up-regulate the expression of TIMP-1. In another aspect, compared with the skin cells only treated with PMA (line 2), the skin cells treated with 6-DG have up-regulated expression level of TIMP-1, and down-regulated expression level of MMP-1, and less phosphorylation level of c-Jun and ERK. In yet another aspect, compared with the skin cells only treated with PMA (line 2), the skin cells treated with PMA prior to being treated with 6-DG have down-regulated expression level of MMP-1 and less phosphorylation level of c-Jun and ERK. It is learned that 6-DG is able to reverse the signal-transduction pathway that PMA phosphorylates JNK and ERK and MMP-1 is expressed. In other words, 6-DG can suppress the phosphorylation of JNK and ERK and inhibit the production of MMP-1.

As the foregoing results, 6-DG is proven to able to inhibit the phosphorylation of JNK and ERK, and reduce the expression of MMP-1.

EXAMPLE 7

Amount of Collagen

Sirius red collagen staining is performed to analyze the effect on the collagen expression of skin cells treated with 6-DG 6-DG of different concentration is added to a 24-well culture dish cultured with human fibroblasts. Medium in the dish is removed and the fibroblasts are washed with PBS twice. 100 µl Sirius Red is added to each well of the dish and incubated at room temperature for 1 hr. After removing the unstained Sirius Red, the fibroblasts are washed with 100 µl 0.1N HCl for at least five times, and then 100 µl 0.1N NaOH is used to extract the stained Sirius Red. Finally, the OD value of the extracted stained Sirius Red is calculated by 540 nm-wavelength light. As the described in "BACKGROUND OF THE INVENTION," it is said that PMA, an activator for protein kinase C, phosphorylates JNK and ERK to produce MMP-1, and inhibits TIMP-1. With regard to the effect on the collagen expression of skin cells treated with 6-DG, the human fibroblasts are incubated with 20 ng/ml PMA prior to being incubated with 6-DG.

Figure 5A:
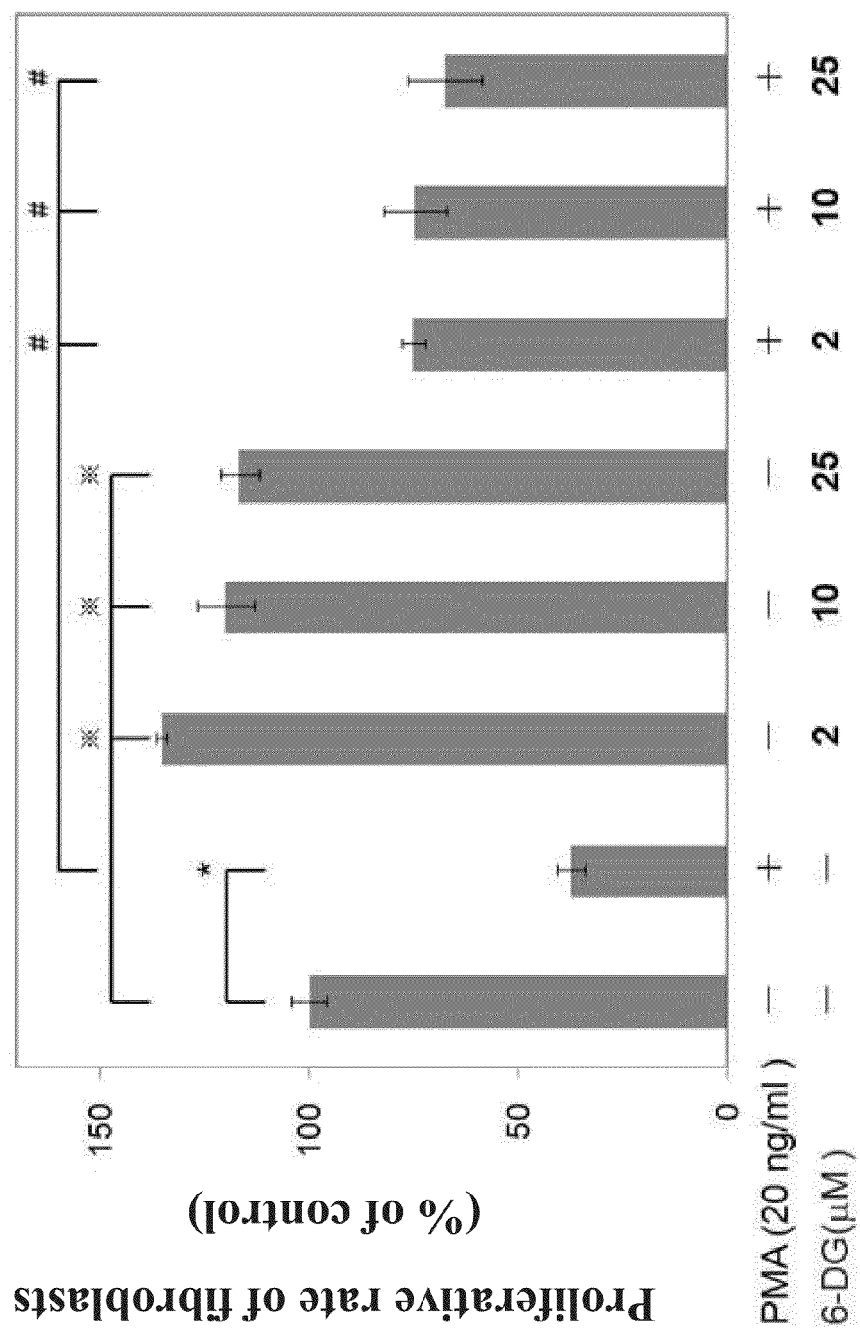
FIG. 5(A) is a bar chart illustrating the proliferative rate of human fibroblasts treated with different concentration of 6-DG.
Figure 5B:
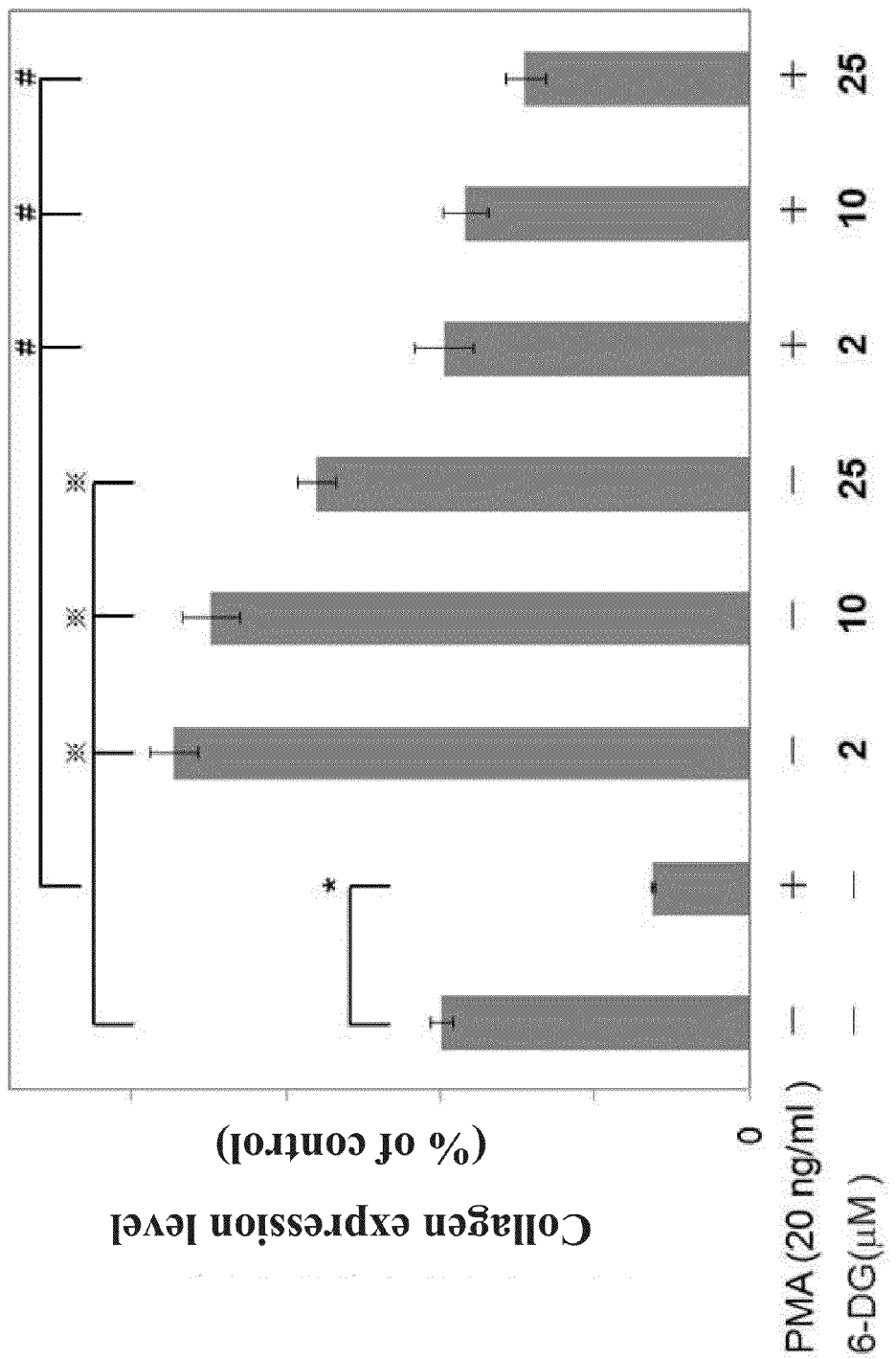
FIG. 5(B) is a bar chart illustrating the collagen expression level of human fibroblasts treated with different concentration of 6-DG.
Figure 5C:
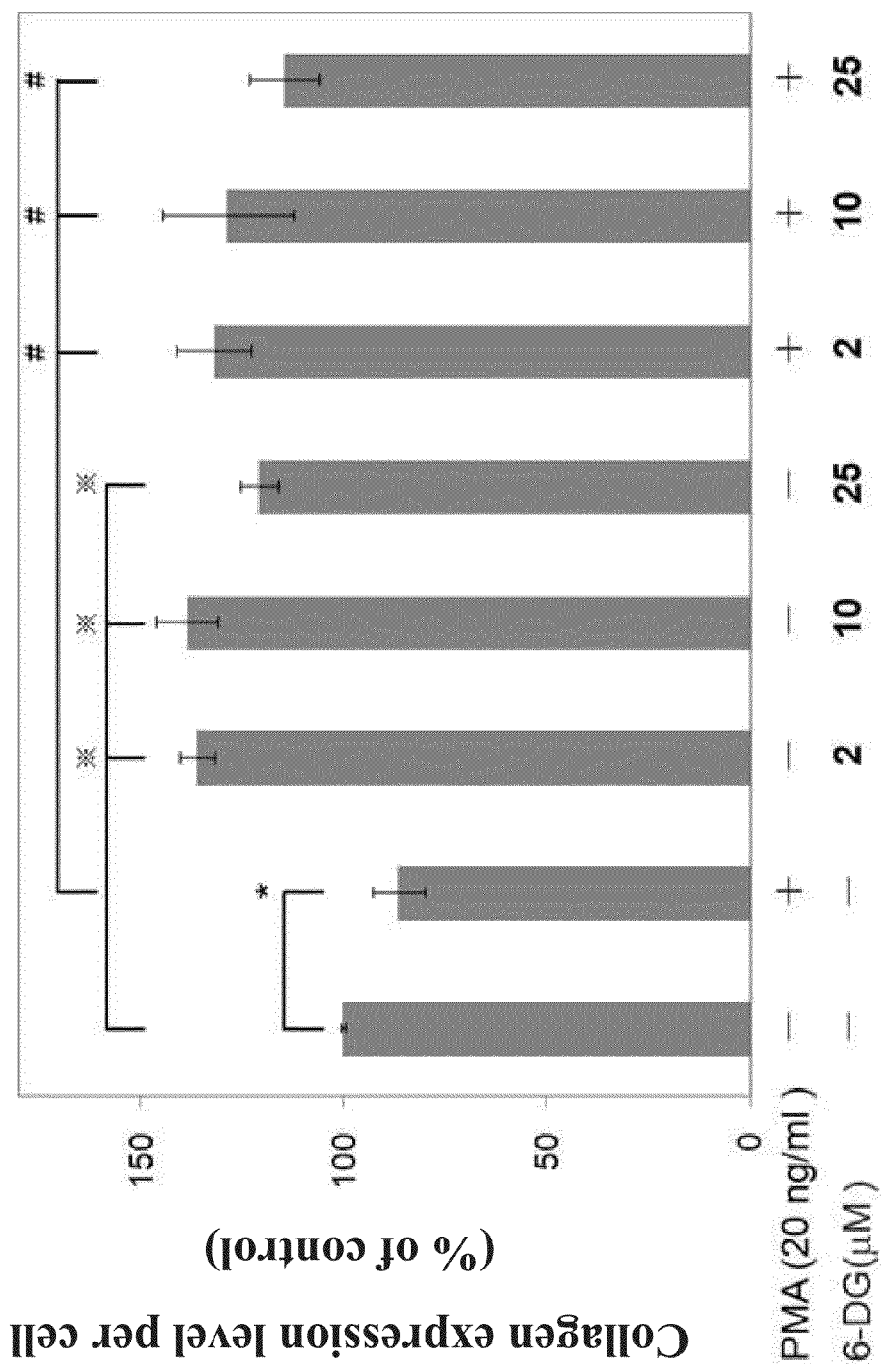
FIG. 5(C) is a bar chart illustrating the collagen expression level per human fibroblast.

As shown in FIG. 5(A), compared with the fibroblasts untreated (control) and those only treated with PMA, the fibroblasts treated with 6-DG have obvious proliferation. In another aspect, compared with the fibroblasts only treated with PMA, the fibroblasts treated with PMA prior to being treated with 6-DG still have obvious proliferation. As shown in FIG. 5(B), compared with the fibroblasts untreated (control) and those only treated with PMA, the fibroblasts treated with 6-DG have up-regulated expression of collagen. In another aspect, compared with the fibroblasts only treated with PMA, the fibroblasts treated with PMA prior to being treated with 6-DG still have up-regulated expression of collagen. As shown in FIG. 5(C), compared with each of the fibroblasts untreated (control) and that only treated with PMA, each of the fibroblasts treated with 6-DG has up-regulated expression of collagen. In another aspect, compared with each of the fibroblasts only treated with PMA, each of the fibroblasts treated with PMA prior to being treated with 6-DG still has up-regulated expression of collagen. It is learned that 6-DG is able to reverse the phenomenon that PMA down-regulates the collagen expression and inhibits the proliferation of fibroblasts. In other words, 6-DG can promote the expression of collagen and the proliferation of human fibroblasts.

As the foregoing results, 6-DG is proven to able to promote the expression of collagen and the proliferation of skin cells.

EXAMPLE 8

Activity of MMP-1

Collagen zymography is performed to analyze the effect on the MMP-1 activity of skin cells treated with 6-DG. After electrophoresis of the foregoing lysed cell extract in SDS-PAGE containing 0.1% collagen, the SDS-PAGE is reacted with 2.5% Triton X-100 to remove SDS and make the protein of the lysed extract folded, and then incubated with a Tris-base buffer containing NaCl, $CaCl_2$, and $ZnCl_2$. Finally, this gel is stained with Coomassie Brilliant Blue R250, and the signal at 52 kDa (molecular weight of collagen) position on the gel is calculated by Gel Pro v4.0 software (Media Cybernetics, Silver Spring, Md., USA).

"BACKGROUND OF THE INVENTION" of the content is said that PMA, an activator for protein kinase C, phosphorylates JNK and ERK to produce MMP-1, and inhibits TIMP-1. For confirming the effect on the MMP-1 activity of skin cells treated with 6-DG, the human fibroblasts are incubated with 20 ng/ml PMA prior to being treated with 6-DG.

Figure 6A:
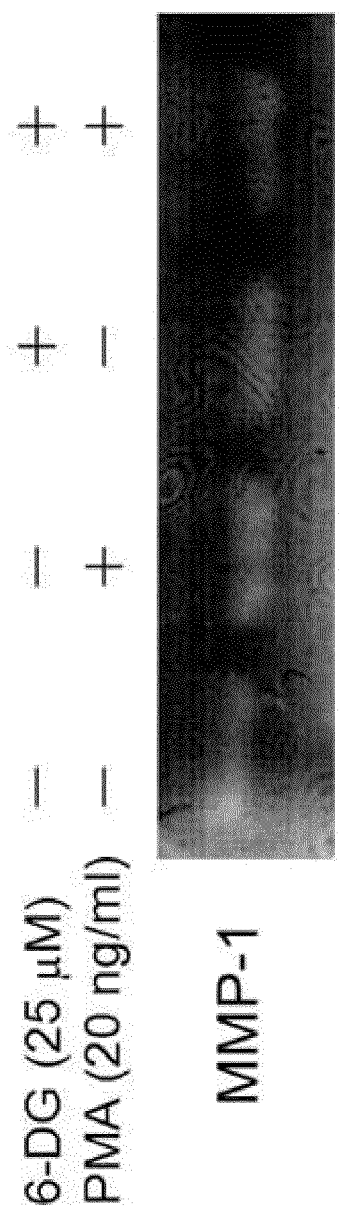
FIG. 6(A) is a picture showing the MMP-1 activity of human fibroblasts treated with 6-DG.
Figure 6B:
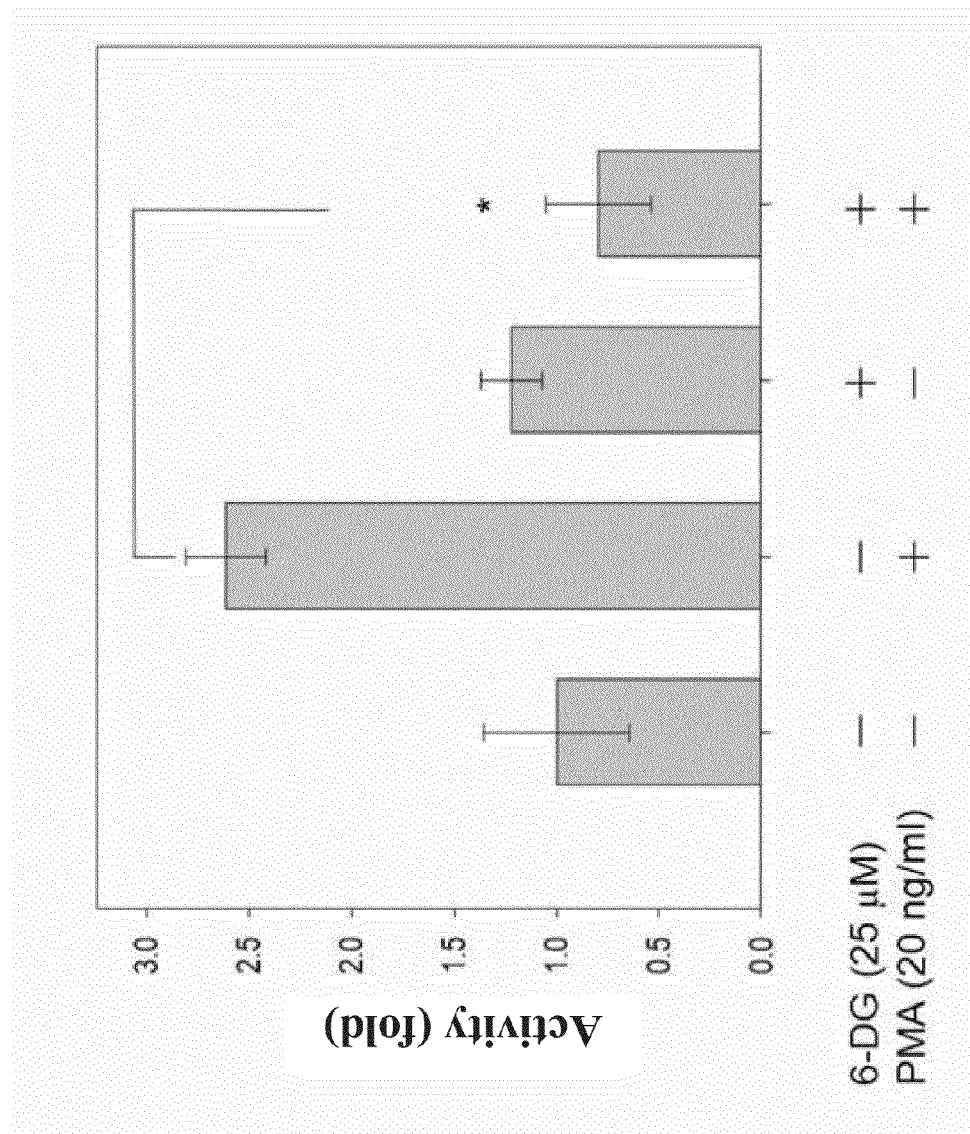
FIG. 6(B) is a bar chart illustrating the MMP-1 activity of human fibroblasts treated with 6-DG.

As shown in FIGS. 6(A) to 6(B), compared with the fibroblasts untreated, the fibroblasts treated with 6-DG have no obvious difference in the activity of MMP-1. In another aspect, compared with the fibroblasts only treated with PMA, the fibroblasts treated with 6-DG have lower MMP-1 activity. In yet another aspect, compared with the fibroblasts only treated with PMA, the fibroblasts treated with PMA prior to being treated with 6-DG have lower activity of MMP-1. It is learned that 6-DG is able to reverse the phenomenon that PMA promotes the production of MMP-1 and the degradation of collagen. In other words, 6-DG can inhibit the production of MMP-1 and induce the expression of collagen.

As the foregoing results, 6-DG is proven to able to inhibit the production of MMP-1 and induce the expression of collagen.

EXAMPLE 9

Statistical Analysis

All data values in the foregoing examples are presented as mean values (±SD) of at least three independent experiments. Data are analyzed by the Student's t test, and statistical significance is assumed of a p value of less than 0.05.

While the invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A method for promoting proliferation and/or migration of skin cells, comprising:

providing a composition containing a compound of formula (I):

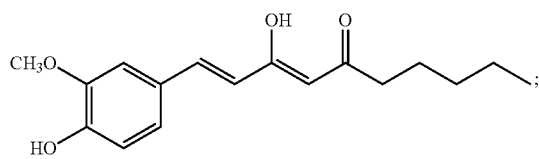

and
administrating to the skin cells said composition.

2. The method as claimed in claim 1, wherein the composition inhibits activity and/or synthesis of matrix metalloproteinase in the skin cells.

3. The method as claimed in claim 1, wherein the composition inhibits phosphorylation of mitogen-activated protein kinase in the skin cells.

4. The method as claimed in claim 1, wherein the composition promotes expression of transforming growth factor-$\beta$, vascular endothelial growth factor, or platelet-derived factor-$\alpha\beta$ in the skin cells.

5. The method as claimed in claim 1, wherein the composition is a ginger extract.

6. A method for improving wound healing in a subject, comprising:

providing a composition containing a compound of formula (I):

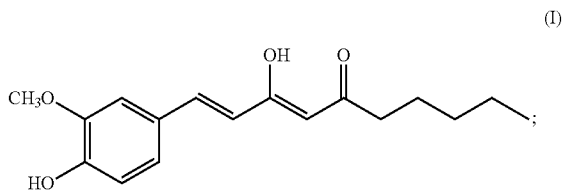

and
administrating to the subject said composition.

7. The method as claimed in claim 6, wherein the composition is a ginger extract.

8. The method as claimed in claim 1, wherein an effective concentration of the compound is 2-50 $\mu$M.

9. The method as claimed in claim 6, wherein an effective concentration of the compound is 2-50 $\mu$M.

* * * * *